United States Patent [19]

Lang et al.

[11] 4,403,841
[45] Sep. 13, 1983

[54] APPARATUS FOR EXAMINING ANTERIOR PORTIONS OF THE EYE

[75] Inventors: Walter H. Lang; Franz Muchel, both of Konigsbronn, Fed. Rep. of Germany

[73] Assignee: Carl Zeiss-Stiftung, Oberkochen, Fed. Rep. of Germany

[21] Appl. No.: 206,076

[22] Filed: Nov. 12, 1980

[30] Foreign Application Priority Data

Nov. 17, 1979 [DE] Fed. Rep. of Germany ....... 2946451

[51] Int. Cl.³ ............................................... A61B 3/10
[52] U.S. Cl. .................................... 351/215; 351/206; 351/221
[58] Field of Search .................... 350/12, 13; 351/6, 8, 351/16, 206, 215, 221

[56] References Cited

U.S. PATENT DOCUMENTS 3,850,527  11/1974  Winthrop et al. ................ 350/13 X Primary Examiner—F. L. Evans
Attorney, Agent, or Firm—Hopgood, Calimafde, Kalil, Blaustein & Judlowe

[57] ABSTRACT

The invention provides an ophthalmological technique and instrumentation for making better and more facile examinations of the anterior portion of an eye, by employing a known interference-contrast technique in on-axis combination with an illumination-source, and having the feature of binocular-microscope viewing. In the form described, polarized light from the source is introduced to the microscope-objective axis at a location between a Nomarski prism and the associated analyzer of the interference-contrast system. This polarized light passes through the Nomarski prism and the microscope objective enroute to the eye being examined; from the eye, it is reflected back through said objective and prism to the analyzer, where a beam-splitting prism serves the respective ray paths of a binocular-microscope viewing system.

2 Claims, 5 Drawing Figures

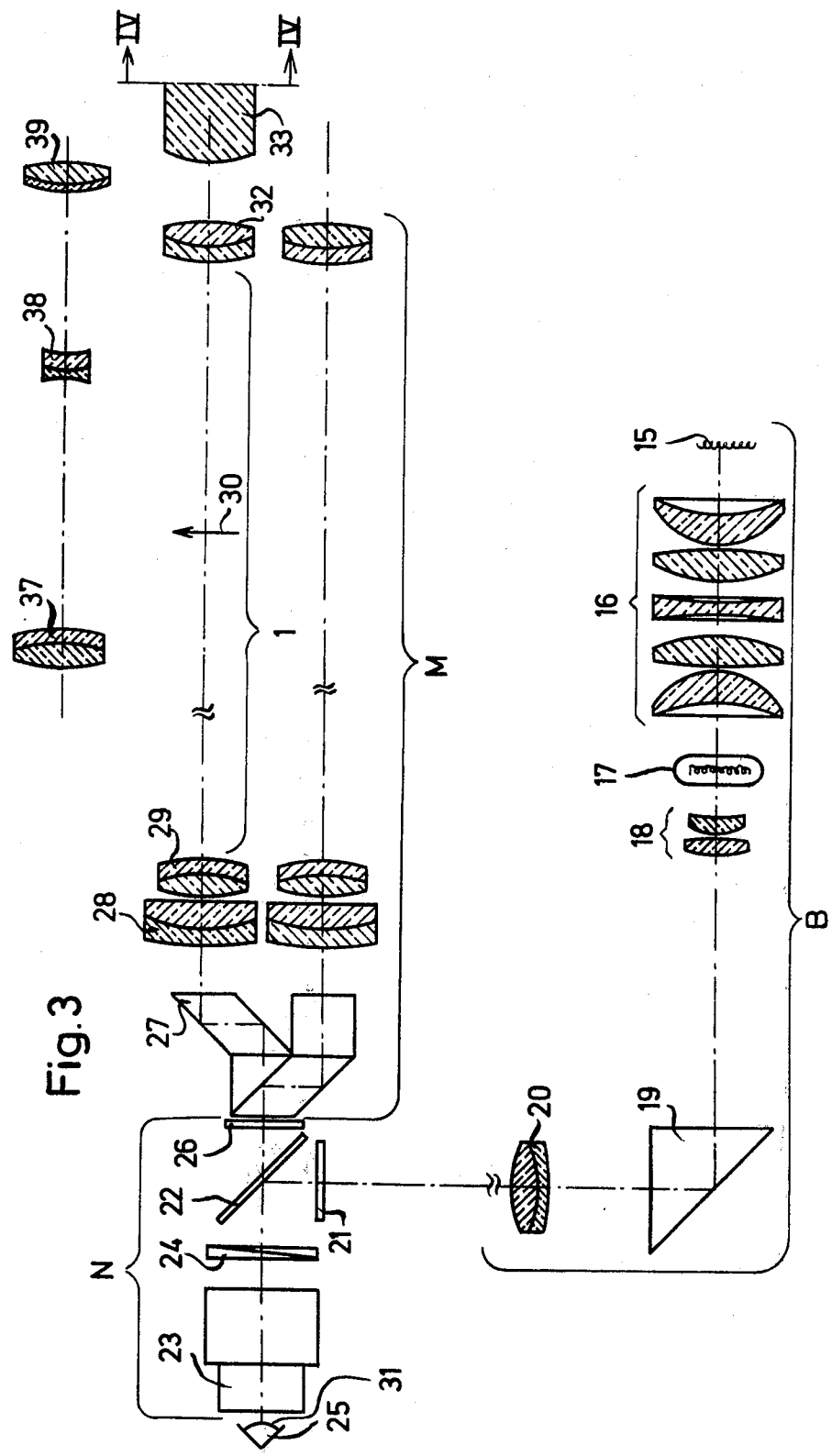

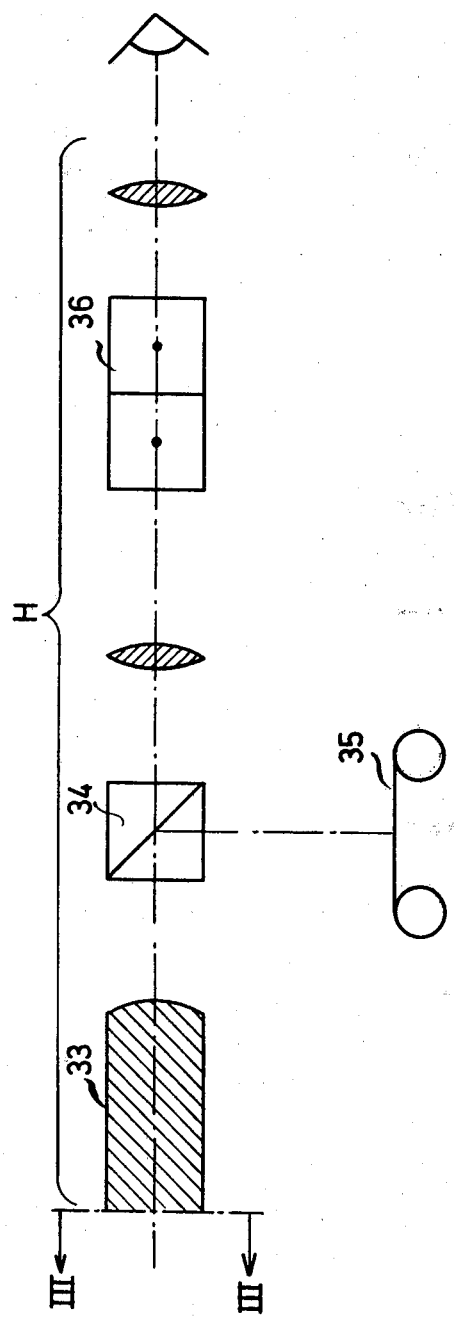

APPARATUS FOR EXAMINING ANTERIOR PORTIONS OF THE EYE

BACKGROUND OF THE INVENTION

The present invention concerns a method for examining anterior portions of the eye and to apparatus for performing the method.

The anterior portions of the eye comprise the cornea, the anterior chamber and the eye lens, and for their examination the use of slit-lamp devices is customary. Such slit-lamp devices consist essentially of an illumination device producing a slit image, and an observation microscope which is normally a stereomicroscope, known as a corneal microscope. The illuminating device which produces the slit image and the corneal microscope are customarily swingable jointly and individually around a vertical axis of rotation. In order to detect opacity or fine foreign bodies in the anterior media of the eye, the slip lamp is generally adjusted oblique to the direction of observation so that light of the slit beam may be dispersed by inhomogeneities of the eye and so that the latter may then be viewable via the corneal microscope. The eye presents itself to the examiner as if the slit-lamp illuminating device had placed a light section through the anterior media, in the direction of the light beam.

BRIEF STATEMENT OF THE INVENTION

The object of the invention is to increase the possibilities of diagnosis for anterior portions of the eye by providing a further examination technique.

The invention achieves this object by employing means whereby a known interference-contrast method may be utilized in diagnostic examination of anterior portions of the eye. By means of an interference-contrast method, very slight differences in phase objects can be represented. And an eye which is examined in this manner presents itself to the examiner as though a section plane of light had been placed transversely through anterior media of the eye.

In one suitable device for performing the method, an interference-contrast device, together with a corneal microscope, and an illumination device are mounted swingably around a common axis of rotation on an ophthalmological examination station.

A headrest for the patient and an instrument base with selectively operable horizontal and vertical adjustment devices for the examining instrument are advantageously provided on the ophthalmological examination station.

In one suitable embodiment of the invention, the optical part of the examination instrument consists of the combination of a known illumination group with a known interference-contrast group, a known corneal microscope, and a new optical-interface part.

An illustrative optical-interface part comprises an image-splitting prism arranged behind the analyzer of the interference-contrast group and, in each of the binocular ray paths, a lens of infinite focal length (for aberration correction) and two objectives; the first of these two objectives supplies a real, erect image of the object to be examined, which is focused at infinity by the second objective.

If a lower overall magnification is desired, the second objective is replaced by a telephoto system with field lens.

The particular advantages of the invention are that, as a result of the transverse light section through front media of the eye, the apparatus is easier and faster to handle than, for instance, a slit-lamp apparatus, and that it also affords better possibility of orientation. Furthermore, the strong light reflection which occurs on the cornea, which for instance is very disturbing in slit-lamp microscopy, is suppressed by the polarization filter provided in the interference-contrast method. Finally, the possibility of representing very slight differences in phase objects can open up new methods of diagnosis.

DETAILED DESCRIPTION

An illustrative embodiment of the invention will be described in detail in conjunction with the accompanying drawings, in which:

FIG. 3 is a diagrammatic view of optical parts of the examining instrument, the ocular connection being broken at IV—IV;

FIG. 3a is a diagrammatic view of the assemblies which, in case of lower magnification, replace the objective 32 of FIG. 3; and FIG. 4 is a diagrammatic view of a known ocular head, shown broken at III—III for connection at IV—IV of FIG. 3.

Figure 1:
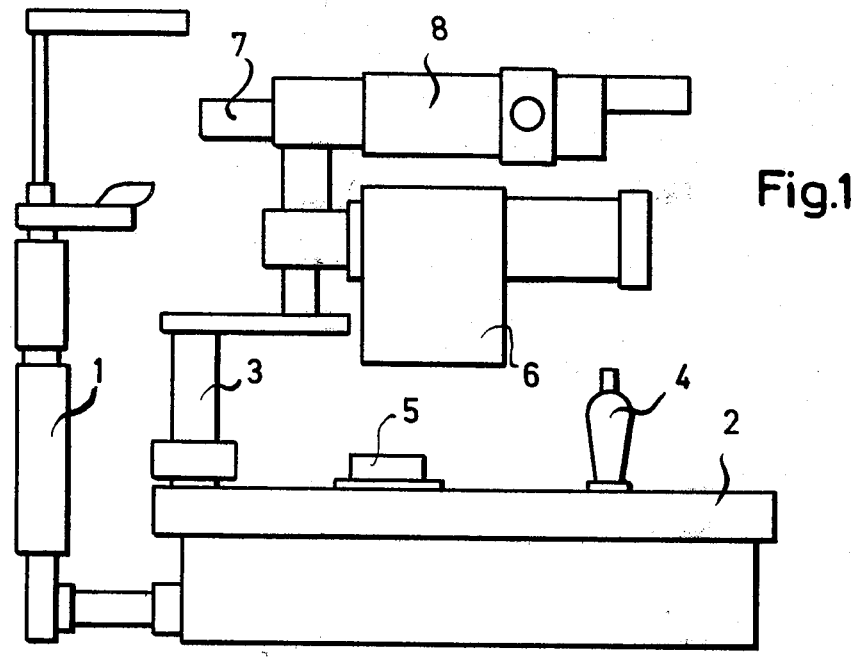
FIG. 1 is a simplified side view of an examining instrument of the invention.

In FIG. 1, the reference numeral 1 designates a head rest for the patient. An instrument base is designated 2 and is provided with a control lever 4 for displacing the examining instrument in a horizontal direction and with a rotary knob 5 for vertical adjustment of the examining instrument. The objects of an interference microscope is designated 7, and numeral 8 identifies a binocular observation device with possibilities of adaptation for joint observation and documentation. An illumination group for visual observation and for documentation is provided at 6. The examining instrument is swingable about a vertical axis of rotation on a column 3.

Figure 2:
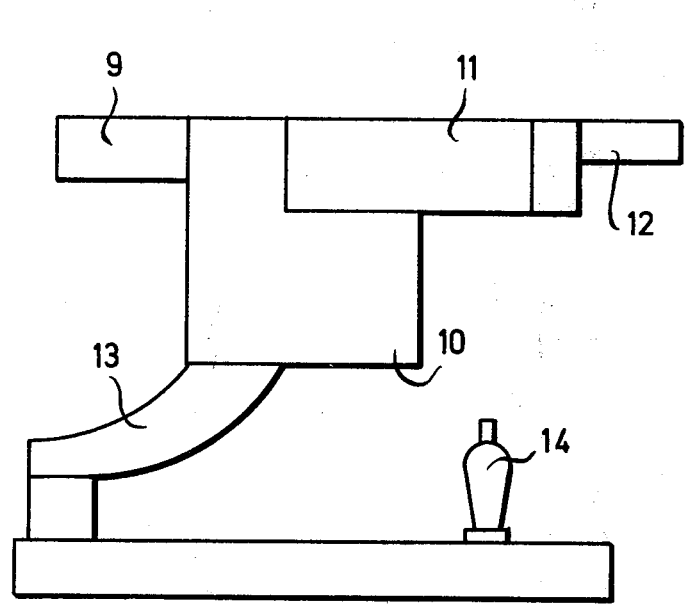
FIG. 2 is a diagrammatic showing of the individual assemblies of the examining instrument, seen in side view.

In the FIG. 2 diagrammatic showing of assemblies, 9 is the objective group, 10 the illumination group, 11 the observation system, 12 an ocular head with binocular viewing, 13 an elevation/swivel drive, and 14 a control lever, with a camera exposure-release button.

In the FIG. 3/FIG. 4 diagrammatic showing of optical construction of the examining instrument, an incandescent lamp 15 (for visual observation) is imaged in the illumination group B via a double collector 16 into an electronic flash tube 17 for photography. In front of the collector 18, a slit system (not shown) is arranged. Lamplight passes, via a reflection prism 19 and an objective 20, through a polarizer 21 and, via a beam-splitting mirror 22, through a Nomarski prism 24 associated with a microscope objective 23, whence it passes to the eye 25 to be examined; objective 23 serves for differential interference-contrast microscopy, and is provided with a screw thread for easy replaceability. Light reflected by the eye 25 passes through an interference-contrast group N, comprising the microscope objective 23, the Nomarski prism 24, the beam-splitting mirror 22 and arrives at an analyzer 26.

In the observation-ray part of the instrument, an optical-interface group M is interposed between the interference-contrast group N and a cornea-microscope group H. In the interface group M, an image-splitting prism 27 is shown rotated 90° in the diagram, in order to show that prism 27 supplies the two separate observation ray paths involved in binocular viewing. Each of these observation ray paths includes a lens group 28 having the focal length $f = \infty$ which serves for correction of aberrations, and behind each correction lens 28 is an objective 29 which supplies a real, erect intermediate image 30 of the object 31 to be examined; a second objective 32 focuses each intermediate image 30 at infinity, and behind objective 32 is a known pancratic system 33 for continuous variation of magnification. In front of and behind the pancratic system, there is a parallel-ray path. A divider cube 34 deflects one part of the light onto a documentation device 35 and the remaining fraction part of the light onto a binocular head 36 for direct viewing.

FIG. 3a shows a telephoto system 38-39 (with field lens 37) which can be used instead of the objective 32, as when only slight magnification is desired. For example, the system with objectives 29-32 gives a magnification factor of 1, and the system with objective 29 and the system 37-38-39 gives a magnification factor of one-half.

We claim:

1. An ophthalmological instrument for examination of anterior regions of an eye, comprising a binocular microscope, and a base establishing a vertical axis of rotary support for said microscope, said microscope including an objective offset from said rotary axis, and the microscope axis through said objective being aligned for intersection with said rotary axis, said microscope including a beam-splitter serving the respective binocular paths thereof from said microscope axis and said microscope also including in each of its binocular paths a first objective producing an intermediate image and a second objective focusing said intermediate image at infinity, a source of polarized illumination and optical elements directing its polarized light onto the microscope axis and in the direction of said objective at a location between said objective and said beam-splitter, a Nomarski prism interposed between said objective and the location of source-light introduction to the microscope axis, and an interference-contrast resolver interposed between said location and said beam-splitter.

2. An apparatus for the examination of the eye consisting of an illumination group (B) and a cornea microscope (H), characterized in that between the illumination group (B) and the patient's eye (25) a polarizer (21), a Nomarski-prism (24) and a microscope objective (23) are arranged and that light reflected by the patient's eye (25) passes through the microscope objective (23), the Nomarski-prism (24) and an analyzer (26) to an optical interface part (M) which is arranged in front of the cornea microscope (H) and which produces an intermediate image (30).

* * * * *